US008146602B2

(12) United States Patent
Cheng

(10) Patent No.: US 8,146,602 B2
(45) Date of Patent: Apr. 3, 2012

(54) METHOD AND MIXTURE FOR NERVE ROOT REPAIR

(75) Inventor: Henrich Cheng, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 1476 days.

(21) Appl. No.: 10/766,530

(22) Filed: Jan. 29, 2004

(65) Prior Publication Data

US 2004/0267289 A1    Dec. 30, 2004

Related U.S. Application Data

(60) Provisional application No. 60/443,167, filed on Jan. 29, 2003.

(51) Int. Cl.
*A61B 19/00* (2006.01)
*A61B 17/08* (2006.01)
*A61B 1/00* (2006.01)
*A61F 2/08* (2006.01)
*A01N 63/00* (2006.01)

(52) U.S. Cl. ........ 128/898; 606/152; 606/213; 606/214; 623/13.17; 424/93.7

(58) Field of Classification Search ................ 606/152, 606/213, 214; 424/93.7; 623/13.17; 128/898
See application file for complete search history.

(56) References Cited

U.S. PATENT DOCUMENTS 4,553,542 A * 11/1985 Schenck et al. ............... 606/153
5,092,871 A * 3/1992 Aebischer et al. ............ 606/152
6,235,041 B1 * 5/2001 Cheng et al. .................. 606/152
6,808,530 B2 * 10/2004 Cheng et al. .................. 606/152
7,141,428 B2 * 11/2006 McKerracher ............. 424/239.1

OTHER PUBLICATIONS

P. M. Yeoman et al., "Brachial Plexus Injuries: Treatment of the Flail Arm", Institute of Orthopaedics, University of London, vol. 43 B, No. 3, Aug. 1961, pp. 493-500.
Thomas Carlstedt, M.D., Ph.D, et al., "Repair of ruptured spinal nerve roots in a brachial plexus lesion", J Neurosurg, vol. 82, pp. 661-7663, Apr. 1995.
T. Carlstedt et al., "Return of function after spinal cord implantation of avulsed spinal nerve roots", The Lancet, vol. 346, pp. 1323-1325, Nov. 18, 1995.
Henrich Cheng et al., "Spinal Cord Repair in Adult Paraplegic Rats: Partial Restoration of Hind Limb Function,", Science, vol. 273, pp. 510-513, Jul. 26, 1995, downloaded from www.sciencemag.org on Aug. 13, 2007.

* cited by examiner

*Primary Examiner* — Gary Jackson
*Assistant Examiner* — Michael Mendoza
(74) *Attorney, Agent, or Firm* — Wolf, Greenfield & Sacks, P.C.

(57) ABSTRACT

The invention provides a method of functionally connecting a portion of the peripheral nervous system of a vertebrate to a portion of the central or peripheral nervous system of said vertebrate, comprising the steps of bringing the portion of the peripheral nervous system and the portion of the central or peripheral nervous system close to each other, applying to the gap between the two portions a fibrin glue mixture comprising a growth factor, fibrinogen, aprotinin and divalent calcium ions so that the fibrin glue mixture is simultaneously in contact with the two portions, and forming an attachment between the portion of the peripheral nervous system and the portion of the central or peripheral nervous system of said vertebrate.

25 Claims, 4 Drawing Sheets
(2 of 4 Drawing Sheet(s) Filed in Color)

A

B

METHOD AND MIXTURE FOR NERVE ROOT REPAIR

This application claims the benefit of provisional application Ser. No. 60/443,167 filed Jan. 29, 2003, the contents of which are expressly incorporated herein.

FIELD OF THE INVENTION

The present invention relates to a method for nerve root repair.

BACKGROUND OF THE INVENTION

A difficult surgical reconstruction problem usually occurring in severe brachial plexus injuries in humans is root avulsion. This type of nerve injury is regarded as a type of central nervous system (CNS) injury not amenable to surgery (Carlstedt et al., 1995, Lancet 346: 1323-1325; Carlstedt et al., J Neurosurg 82(4): 661-663). The divided rootlets at the point of connection with the spinal cord, i.e., the ventral entry zone (VREZ) and the dorsal rootlet entry zone (DREZ), may withdraw to a large extent (before the decision to operate has been made several weeks after the injury), making direct repair by repositioning difficult (Narakas, 1987, Orthopade 16(1): 81-86). Many previous studies (in humans, non-human prima and other mammals) show that sectioned peripheral axons of one never can regenerate through foreign nerves to reinnervation different motor of sensory fields. In 1961, Seddon reinnervated the biceps and the brachialis muscles by anastomosing the distal part of the musculocutaneous nerve with the second, third and fourth intercostals nerves (Yeoman and Seddon, 1961, J Bone Joint Surg 43B: 493.499). In addition, nerve transfer, which is called as "neurotization" with interostals or other nerves, including spinal accessory nerves and anterior nerves of the cervical plexus, has also been reported to lead to some positive clinical results (Kotani et al., 1972, Excerpta Med Int $12^{th}$ Congress Series 291: 348-350; Brunelli and Brunelli, 1980, In Surg 65(6): 529-531). However, these types of surgeries were still in experimental phase and suffered from lack of fundamental knowledge (Narakas 1987). Neither of the above-mentioned reports demonstrated a functional recovery of the treatment of root avulsion.

Recently, direct reconstruction of connectivity between the spinal cord and the nerves after spinal nerve root injury has also been demonstrated (Cullheim et al., 1989, Neuroscience 29: 725-733; Carlstedt et al., 1990, Restor Neurol Neurosci 1: 289-295; Carlstedt et al., 1993, J Neurol Neurosurg Psychiatry 56: 649-654; Smith and Kodema, 1991, Brain res Bull 30: 447-451). This kind of approach is more capable to bring the reconstructed neural networks close to the original statues. However, is clinical practice, it is difficult to find and approximate the retracted ends of the avulsed roots within 2-3 months after the injury, which is the minimum time period necessary to verify a real neurotemesis (Leffert, 1983, Schmidek H H, Sweet W H, eds. Operative Neurosurgical Techniques. Orlando: Grune & Stratton, 1495-1540). In most cases, this fact hinders the attempt to reinsert the avulsed roots to the spinal cord. However, there is no evidence showing that long-term regeneration supporting wrist or hand functions has been established. A repair of complete transection of the spinal cord in rats with a fibrin glue containing acidic fibroblast growth factor (aFGF) has been reported (Chang et al., 1996, Science 273: 510-513). However, no successful treatment for avulsion of nerve roots at their junction with the spinal cord has been reported.

In view of the above, new and effective strategies for repairing nerve root avulsion are desired.

SUMMARY OF THE INVENTION

The invention is based on the discovery that avulsions between the central and peripheral nervous systems can be repaired using a fibrin glue mixture to restore the functional connection of the avulsed ends.

Accordingly, the invention features a method of functionally connecting a portion of the peripheral nervous system of a vertebrate to a portion of the central or peripheral nervous system of said vertebrate, comprising the steps of bringing the portion of the peripheral nervous system and the portion of the central or peripheral nervous system close to each other, applying to the gap between the two portions a fibrin glue mixture comprising a growth factor, fibrinogen, aprotinin and divalent calcium ions so that the fibrin glue mixture is simultaneously in contact with the two portions, and forming an attachment between the portion of the peripheral nervous system and the portion of the central or peripheral nervous system of said vertebrate.

More specifically, the invention features a method of functionally connecting a portion of the peripheral nervous system of a vertebrate to a portion of the central nervous system of said vertebrate, comprising the steps of bringing the portion of the peripheral nervous system and the portion of the central nervous system close to each other, applying to the gap between the two portions a fibrin glue mixture comprising a growth factor, fibrinogen, aprotinin and divalent calcium ions so that the fibrin glue mixture is simultaneously in contact with the two portions, and forming an attachment between the portion of the peripheral nervous system and the portion of the central nervous system of said vertebrate.

In particular, the present invention features a method of functionally reconnecting an avulsed nerve root to the spinal cord to be connected in a vertebrate, comprising the steps of bringing the avulsed nerve root close to the spinal cord, applying to the gap between the nerve root and the spinal cord a fibrin glue mixture comprising a growth factor, fibrinogen, aprotinin and divalent calcium ions so that the fibrin glue mixture is simultaneously in contact with the nerve root and the spinal cord, and forming an attachment between the nerve root and the spinal cord of said vertebrate. In one specific embodiment, the avulsed nerve root is an avulsed cervical root.

The invention also features a method of functionally connecting two portions of the peripheral nervous system of a vertebrate, comprising the steps of bringing the two portions of the peripheral nervous system close to each other, applying to the gap between the two portions a fibrin glue mixture comprising a growth factor, fibrinogen, aprotinin and divalent calcium ions so that the fibrin glue mixture is simultaneously in contact with the two portions, and forming an attachment between the two portion of the peripheral nervous system of said vertebrate.

In particular, the present invention features a method of functionally connecting the proximal and distal ends of a peripheral nerve in a vertebrate, comprising the steps of bringing the two ends to each other, applying to the gap between the two ends a fibrin glue mixture comprising a growth factor, fibrinogen, aprotinin and divalent calcium ions so that the fibrin glue mixture is simultaneously in contact with both ends, and forming an attachment between the proximal and distal ends of the peripheral nerve in said vertebrate. In one specific embodiment, the peripheral nerve is a sciatic nerve.

The method of the present invention may further comprise the step of suturing or anastomosing the two portions of the nervous system to be connected.

The method of the present invention may further comprise the step of introducing a tissue graft to the gap between the two portions of the nervous system to be connected. In one specific embodiment, the tissue graft is a sural or intercostal nerve of said vertebrate.

According to the invention, the fibrin glue mixture comprises acidic fibroblast growth factor, fibrinogen, aprotinin and divalent calcium ions.

BRIEF DESCRIPTION OF THE DRAWINGS

The patent or application file contains at least one drawing executed in color. Copies of this patent or patent application publication with color drawings will be provided by the Office upon request and payment of the necessary fee.

A-D: Consecutive photos take from digital videotape of a group C1 rat whose left forepaw could not extend and support its body weight in walking.

E-H: Consecutive photos taken from digital videotape of a group E rat showing that the left few can fully extend and support its body weight in walking.

I-K: Photographs of the result of the grooming test

I: A group C1 rat, showing a grade 0 grooming reflex in the left forelimb,

J: A group C2 rat showing a grade 1 grooming reflex in the left forelimb.

K: A group E rat, showing a grade 4 grooming reflex in the left forelimb.

L: The result of the grooming test thee months postoperatively. Group E showed improvement corn with groups C1 and C2. Significant test between C1/E (Mann-Whitney Test, p=0.0039) and C2/E (M-W Test, p=0.0051, error bar: one standard error)

Figure 2:
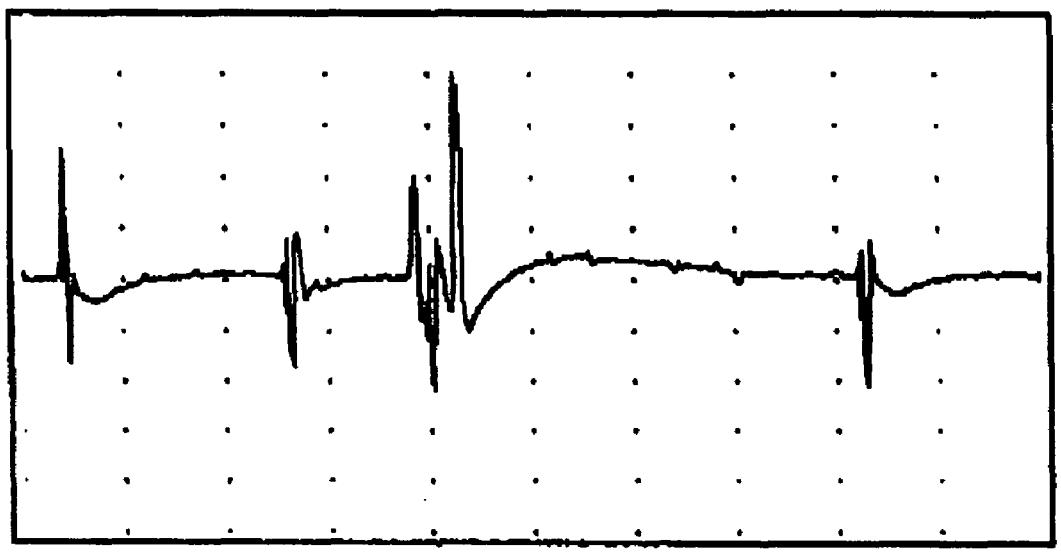
Figure 2:

FIG. 2 shows the results of electromyography for evaluation of the tonal recovery after repairs of the avulsed cervical roots.

A. Spontaneous activities (fibrillations, Grade 4+) of biceps brachii in the semi-sedated rat of Croup C2 6 weeks postoperatively. (sweep speed. 200ms/div; amplitude, 50 μV/div)

Grading of (fibrillation): 0, no fibrillation potentials; 1+, single trains in at least two muscle regions; 2+, moderate numbers in three or more muscle areas; 3+, many in muscles regions; 4+, in all areas of sampled muscles.

B. Recruitment of motor unit potential in response to biceps brachii minimal contraction in the rat of Group C2, 6 months 0 postoperatively, (sweep speed, 200 ms/div; amplitude. 200 mv/div)

MUP (motor unit potentials), +: polyphasia>20% of sampled motor unit potentials; −: no evidence of polyphasic waves.

Figure 3:
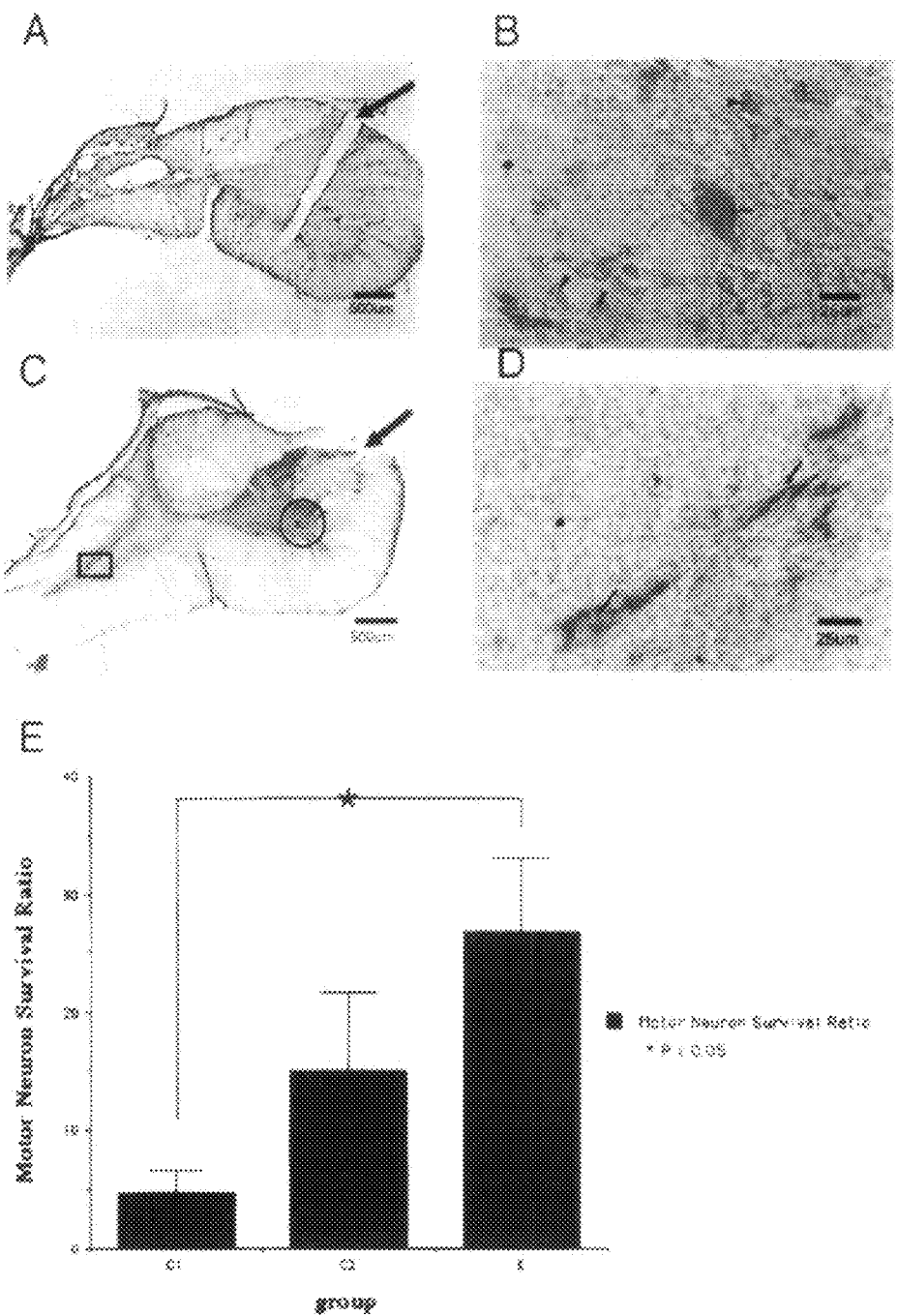

FIG. 3 shows the results of HRP retrograde axonal tracing.

A-D: Photomicrographs of the spinal cord after HRP retrograde axonal tracing.

A: The spinal cord in group C1 was markedly atrophic with cystic degeneration (HRP) Thu unlesioned side is marked (arrow)

B: The same spinal cord of A, with higher magnification, showing that the motor neuron looked swollen with granulation in the cytoplasm (arrow); there is also hemosiderin deposition in the interstitium (arrowhead). (HRP)

C: The spinal cord of group B was less atrophic and showed less cystic degeneration (HRP). Not several labeled neurons in the unlesioned side (circle).

D: The rectangular area in C, with higher magnification, showing the labeled motor neurons was normal in appearance (HRF, X132).

E: The results of motoneuron survival ratio. *The difference between group E and C1 is significant (p=0.0341, ANOVA test). (Error bar: one standard error)

Figure 4:
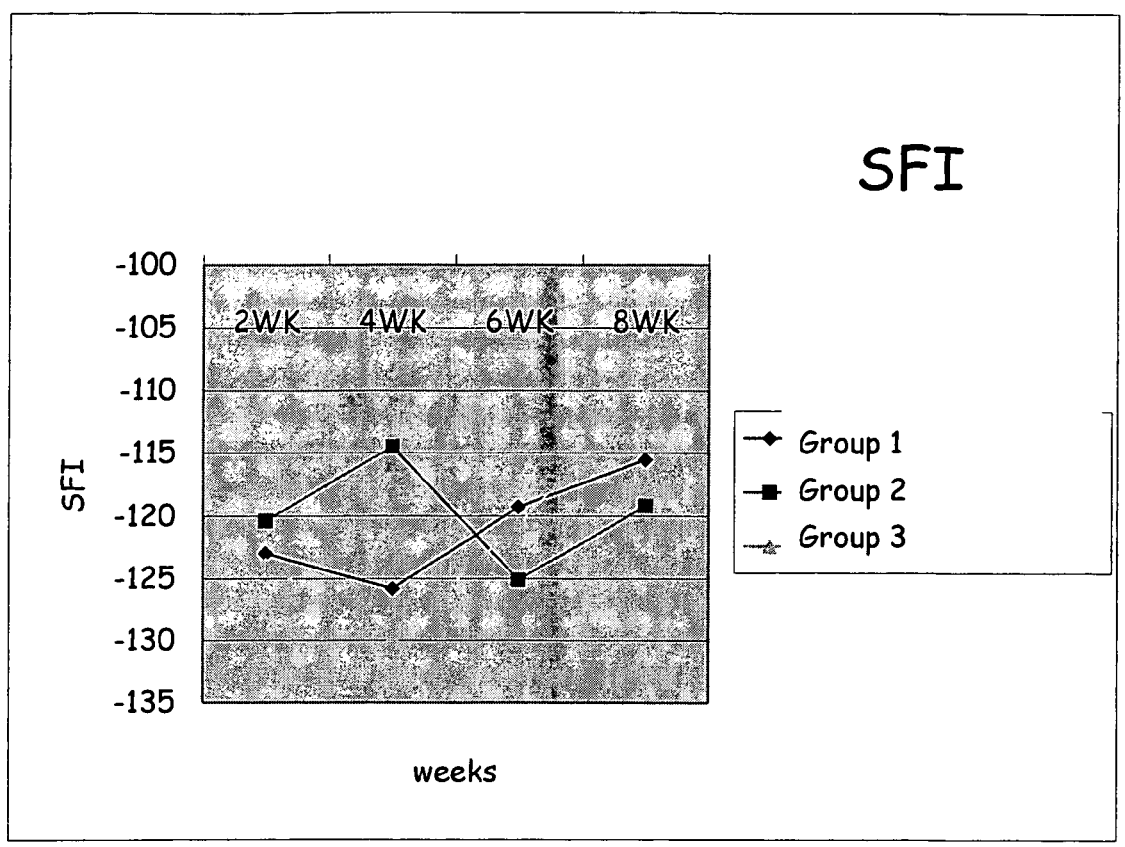

FIG. 4 shows the results of functional recovery after repair of the sciatic nerve injury.

DETAILED DESCRIPTIONS OF THE INVENTION

The invention relates to a method for functionally connecting a portion of the peripheral nervous system of a vertebrate to a portion of the central or peripheral (particularly central) nervous system of said vertebrate with a fibrin glue mixture comprising a growth factor, fibrinogen, aprotinin and divalent calcium ions. According to the invention, the components of the fibrin glue mixture cam be simultaneously or separately applied to the gap between the two portions of the nervous system to be connected.

The growth for used in the method of the present invention is selected from, but not limited to, a glial cell line-derived neurotrophic factor, transforming growth factor-beta, fibroblast growth factor, platelet-derived growth factor, epidermal growth factor, vascular endothelial growth factor (VEGF), and neurotrophin (such as nerve growth factor (NGF), brain-derived neurotrophic factor (BDNF), NT3, NT4 and NT5). More preferable, the growth factor is fibroblast growth factor, including acidic fibroblast growth factor (aFGF) and basic fibroblast growth factor (bFGF). Most preferably, the factor is acidic fibroblast growth factor (aFGF). The concentration of the acidic fibroblast growth factor in the fibrin glue mixture is preferably about 0.0001 to 1000 mg/ml, more preferably 1 mg/ml.

The divalent calcium ions can be any calcium ion sources, such as those provided by addition of calcium chloride or calcium carbonate.

In an embodiment of the invention, the fibrin glue mixture comprises fibroblast growth factor, fibrinogen, aprotinin and calcium chloride. In a preferred embodiment of the invention, the fibrin glue mixture comprises acidic fibroblast growth factor, fibrinogen, aprotinin and calcium chloride. The concentration of fibrinogen in the glue solution is preferably about 10 to 1000 mg/ml, more preferably about 100 mg/ml. The concentration of aprotinin in the glue solution is preferably about 10 to 500 KIU/ml. more preferably 200 KIU/ml. The concentration of calcium chloride in the glue solution is preferably about 1 to 100 mM, more preferably 8 mM.

If necessary, the fibrin glue used in the method of the present invention may be supplemented with other substances for enhancing repair, such as a steroid, e.g. methylprednisone; a cytokine; a chemokine; a proteinase, e.g a metalloproteinase; an extracellular matrix molecule, e.g. laminin or tenascin; a guidance molecule, i.e. a molecule that attracts or repels the migration of a cell, e.g. netrin, semaphorin, neural call adhesion molecule, cadherin, thioredoxin peroxidase or Eph ligand; an anti-angiogenic factor, e.g. angiostatin, endostatin, TNP-470 or kringle 5; a neuroprotective agent, e.g. N-methyl D-aspartate (NMDA), a non-NMDA antagonist, a calcium channel blocker, nitric oxide synthase (NOS), a NOS inhibitor, peroxynitrite scavenger or a sodium channel blocker; and a Nogo gene polypeptide and antibodies that specifically bind to the polypeptide.

The fibrin glue mixture used in the method of the present invention may also optionally include a cell or cell suspension for facilitating repair, such as Schwann cells, bone marrow cells, blood cells, stem cells and olfactory ensheathing glial (OEG) cells.

The present invention is illustrated by the following examples.

EXAMPLES

Examples of the Fibrin Glue Mixture According to the Invention

| Mixture No. | acidic fibroblast growth factor (aFGF) | Fibrinogen | Aprotinin | Calcium Chloride |
|---|---|---|---|---|
| Mixture 1 | 1 mg/ml | 100 mg/ml | 200 KIU/ml | 8 mM |
| Mixture 2 | 10 mg/ml | 1000 mg/ml | 500 KIU/ml | 2 mM |
| Mixture 3 | 50 mg/ml | 500 mg/ml | 10 KIU/ml | 50 mM |
| Mixture 4 | 100 mg/ml | 10 mg/ml | 50 KIU/ml | 100 mM |
| Mixture 5 | 1000 mg/ml | 200 mg/ml | 300 KIU/ml | 80 mM |
| Mixture 6 | 0.001 mg/ml | 20 mg/ml | 20 KIU/ml | 1 mM |

Animal Test (Part D)
Materials and Methods
Animals:

Eighteen female adult 250 g rats (Sprague-Dawley) were used. The animals were operated on a heating pad under general halothane anesthesia (1.5 liters/min to keep the breathing rate at approximately 60/min). Rectal temperatures were monitored and maintained during surgery at no less than 3° C. below normal temperature. Bipolar electrocauterization was used to minimize bleeding. Antibiotics (gentamicin 1.6 mg/100 mg BW) were injected subcutaneously before the operation and once daily for one week afterwards. No infections were encountered. After the operation, animals were kept in ventilated humidity- and temperature-controlled rooms with a 12/12 h light/dark cycle. They received food pellets and water ad libitum. The local Ethical Committee for Animal Research of Taipei approved all experiments.
Repair of the Transected Cervical Root:

The rats were placed in a prone position and their C2-C7 vertebrae were exposed. Left C5 to C6 hemilaminectomies were carried out. While under the microscope, the left C6 and C7 cervical roots were identified and followed after the overlying facets had been removed by drilling slightly more laterally in these segments. The dura was then carefully opened and the C6 and C7 nerve roots were pulled tight and transected at their junction with the cervical cord. No visible proximal stumps remained in these roots. Six rats (the first control group, C1) were subjected to the above procedures only. For reconstruction, two autologous intercostal nerves were harvested and preserved in Hanks' balanced salt solution. One end of the intercostal nerve was anastomosed microscopically to the severed root by 10-0Nylon (FSSB, Germany) in an end-to-end fashion. The other end of the intercostal nerve was then approximated to the cord through a tiny pia incision, ventral to the dentate ligament. The fibrin glue mixture lacking a growth factor was prepared before use by mixing the fibrinogen (100 mg/ml) with Apotinln solution (200 KIU/ml) plus calcium chloride (8 mM) in the surgical area to form a glue cast. The final volume of the mixture was about 10 µl. After both nerve roots had been reconnected, fibrin glue was applied to the grated area. Six rats (the second control group, C2) were subjected to these reconstruction procedures. Experimental rats (E, n=6) were subjected to the above reconstruction with the fibrin glue mixture with adding 10 µg of aFGF (Recombinant Human FGF, acidic, R&D systems Inc. USA). Animals were randomly assigned to one of the above three groups.
Behavioral Tests:

Trained personnel performed a blind evaluation on all rats for motor activity (including weight bearing and claw extension) and carried out grooming tests at 2, 4, and 8 weeks, and 3 months postoperatively. The animals were allowed to walk across a runway with a semi-transparent floor in order to test motor activity. Special attention was paid to observing whether the rats could extend the fingers of the affected limb as well as to whether they were able to use the affected limb for weight bearing.

The grooming test was performed in the cage by sprinkling water over the rat's head and evaluating the grooming response of the forepaws toward the head. Animals were evaluated carefully for at least five minutes and the maximal abduction for each side of the body was scored. The highest level that one forepaw could reach during the observed period was scored as 0 below the mouth, 1 below the nose, 2 below the eye, 3 below the ear, and 4 when it reached the postauricular region. Normal animals usually scored 3 or above.
Electromyogram (EMG):

Electromyograms were performed 6 weeks and 6 months postoperatively, by recording the activity of the deltoid, biceps and triceps under sedation with sodium pentobarbital (intra-peritoneal 36/mg/kg). Special attention was paid to whether the denervation changed its patterns in accordance with time and whether reinnervation occurred in individual muscles. For detail, refer to Chuang T Y et al., 2002, "Forelimb muscle activity following nerve graft repair of ventral roots in the rat cervical spinal cord." Life Science (in press).
Retrograde Axonal Tracing:

Horseradish peroxidase (HRP) retrograde axonal tracings were performed six months after the operation. HRP (16.7%, dissolved in normal saline) was injected in the rat's deltoid, biceps end triceps bilaterally under sedation with sodium pentobarbital (intra-peritoneal, 36/mg/kg). Forty-eight hours after the injection, the animals were deeply anesthetized with pentobarbitone sodium and perfused intracardially with 37° C. normal saline, followed by 100 cc of 2% phosphate-buffered glutaraldehyde and 4% paraformaldehyde at 4° C. for 15 minutes, and 100 cc of 10% sucrose buffer for 20 minutes. The spinal cords were removed for cryostat sectioning. The cervical cords were cut transversely into serial 40-µm sections. The sections were treated with the diaminobenzidine method before microscopic examinations took place. The numbers of labeled nerve cell bodies were derived by the use of Abercrombie's formula. The survival ratio of the neurons on the affected side for one rat was the percentage of the calculated number of neurons an the left side over the number of neurons on the right side.

Example 1

Functional Recovery After Repair of the Avulsed Cervical Roots

Figure 1:
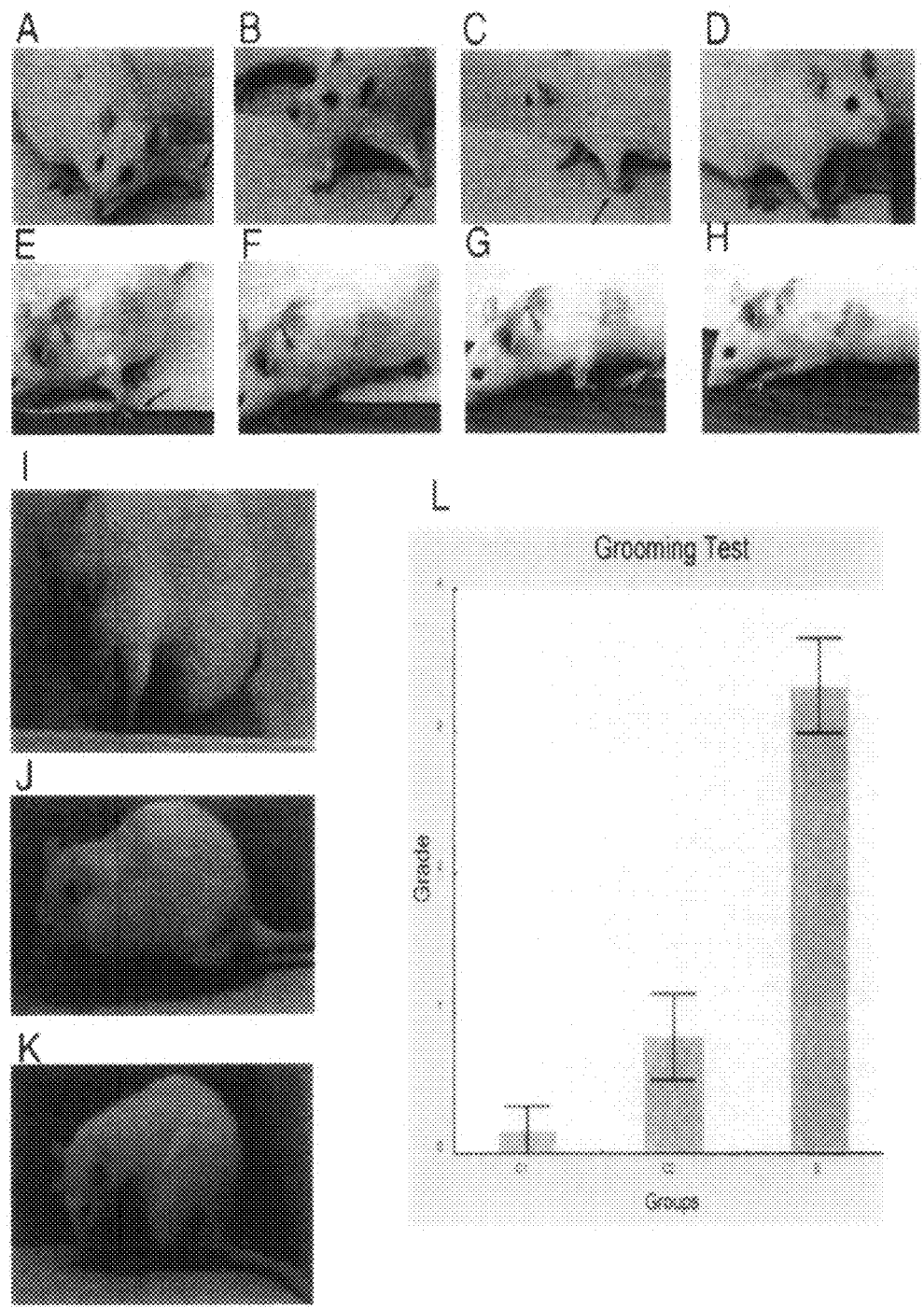
FIG. 1 shows the results of the motor function after repairs of the avulsed Oval A-H: Photographs of the motor recovery. (arrow: lesion limb)

Initially, all groups showed marked paralysis of the left biceps, triceps and intrinsic hand muscles, with claws fixed in a flexed position. All rats lost grooming reflexes, weight bearing ability and claw extension ability of the left forelimb. The rats in the experimental group showed signs of recovery two or tree weeks later. Two months postoperatively, the group's ability to freely move the left elbow progressed, as well as their ability to fully extend claws while reaching for weight bearing (FIG. 1, E-H). In contrast, 3 months after surgery, the group C1 rats had no weight bearing ability and their claws remained curled (FIG. 1, A-D). Two out of six animals in the C2 group displayed some degree of elbow motion recovery at 3 months postoperatively, with partial weight bearing of the left forelimb. The grooming reflex of the repaired left forelimb in five rats from group E recovered to grade 3 or 4, and to grade 2 in another rat at three moths postoperatively. Rats in either grow C1 or C2 had scores below grade 2 (FIG. 1, I-K). The grooming reflex scores were significantly higher in group E than in group C1 or group C2 (FOG. 1, L; p=0.0039 been E and C1, p=0.0051 between E and C2, Mann-Whitney test).

Example 2

Electrophysiological Changes after Repair of the Avulsed Cervical Roots

Functional recovery was evaluated electrophysiologically at 6 weeks and 6 months postoperatively. Needle electromyography showed a profound denervation in the deltoid, biceps and triceps of the operated left forelimbs in all groups at six weeks. At this point, three out of six rats in group E showed signs of regeneration (FIG. 2, A). Two rats in group C2 also showed signs of regeneration. None in group C1 demonstrated signs of regeneration at this time. After 6 months, signs of denervation persisted in three group E rats and four group C2 rats. Electromyographic evidence of regeneration, such as the appearance of giant polyphasic waves together with normalization of membrane instability, was noted in all animals of groups E and C2. All rats in group C1 demonstrated persistent denervation without any sign of regeneration at six months, except for one rat which exhibited small polyphasic waves in m. triceps brachii (FIG. 2, B). For detail, please refer to the manuscript of Chuang T Y et al, 2002.

Example 3

Horseradish Peroxidase (HRP) Retrograde Axonal Tracing

Retrograde axonal tracing with HRP was performed in four group E, three group C1, and three group C2 rats. The spinal cords of animals in group C1 demonstrated severe atrophy with a large cyst present at the affected level (FIG. 3, A). The remaining neurons in the affected area appeared swollen with granules in the cytoplasm (FIG. 3, B). The survival ratio of neurons was 1%, 6% and 7% respectively. The spinal cords of the four rats in group E demonstrated mild atrophic change without cyst formation (FIG. 3, C). Neurons in the affected area were normal in appearance (FIG. 3, D). The survival ratio of neurons was between 16 and 45%. The survival ratio of neurons in group C2 was between that of group E and C1 (2-24%). The difference in motoneuron survival ratio between group E and group C1 was statistically significant (FIG. 3, E; p=0,0341, ANOVA test). The correlation between the motoneuron survival ratio and the grading of the grooming reflex was also significant (single regression test correlation coefficient 0.845).

All results are summarized in Table 1.

The results of the above examples have indicated that motor recovery of the rat's forelimb after cord-root junction transection can be achieved to a satisfactory level through the method of the present invention.

TABLE 1

Data for functional recovery after repairing transected cervical roots

| Number | Group | Behavior (6 M) | | Grooming (6 M) | | (6 M) Motoneuron Survival Ratio | EMG (6 W) | | EMG (6 M) | |
|---|---|---|---|---|---|---|---|---|---|---|
| | | WB | CE | Left | Right | Left/Right (%) | Den | Reg | Den | Reg |
| 1 | E | Y | Y | 4 | 3 | 204/844 (24%) | + | − | − | + |
| 2 | E | Y | Y | 4 | 3 | ND | + | + | − | + |
| 3 | E | Y | Y | 3 | 3 | ND | + | + | − | + |
| 4 | E | Y | Y | 4 | 4 | 160/356 (45%) | + | + | + | + |
| 5 | E | Y | Y | 3 | 3 | 114/528 (22%) | + | − | + | + |
| 6 | E | Y | Y | 2 | 4 | 66/408 (16%) | + | − | + | + |
| 7 | C1 | N | N | 0 | 3 | 32/548 (6%) | + | − | + | − |
| 8 | C1 | N | N | 0 | 4 | 8/576 (1%) | + | − | + | − |
| 9 | C1 | N | N | 0 | 3 | ND | + | − | + | − |
| 10 | C1 | N | N | 0 | 3 | 40/572 (7%) | + | − | + | − |
| 11 | C1 | N | N | 1 | 4 | ND | + | − | + | + |
| 12 | C1 | N | N | 0 | 3 | ND | + | − | + | − |
| 13 | C2 | Y | Y | 1 | 4 | ND | + | + | − | + |
| 14 | C2 | N | N | 0 | 4 | (8/351) 2% | + | + | | + |
| 15 | C2 | N | N | 0 | 3 | ND | + | − | + | + |
| 16 | C2 | N | N | 1 | 3 | 84/351 (24%) | + | − | + | + |
| 17 | C2 | Y | Y | 1 | 4 | 75/402 (19%) | + | − | + | + |
| 18 | C2 | Y | Y | 2 | 4 | ND | + | − | + | + |

WB: weight bearing;
Y: affected limb touches the ground when walking;
N: affected limb does not touch the ground when walking
CE: claw extension;
+: extension of the fingers of the affected limb when weight bearing;
−: no extension of the fingers of the affected limb when weight bearing
Den: denervation;
Reg: regeneration
ND: No data Animal Test (part II)

Example 4

Functional Recovery after Hair of a Sciatic Nerve Injury

The test was performed on our female Sprague-Dawley rats weighed between 280 and 320 g The rats were anesthetized with 1% isoflurane and $O_2N_2O$, and shaved on their right limb. The right sciatic nerve was exposed by splitting the right superficial gluteal muscle, and transected twice in the middle to make a 15 mm-gap.

For the first rat (Group 1), the transected 15 mm-nerve was removed, and a fibrin glue mixture lacking a growth factor prepared as described above in Part I of the animal test was applied to the left gap. For the rest of the rats, the transected nerve was retained and the transected ends were sutured with 10-0 Nylon (FSSB, Germany), and fibrin glue mixtures were applied thereto. The fibrin glue mixture applied to the end and third rat (Group 2) was the same as that applied to the first rat, while the fibrin glue mixture applied to the fourth rat (Group 3) additionally contained 1 μg/μl aFGF. All the above surgical procedures were performed under an operation microscope and a sterile procedure was used.

After the operation, all the four rats received antibiotics via subcutaneous injection, and were kept in ventilated, humidity- and temperature-controlled rooms for recovery. They received food pellets and water ad libitum. Every two weeks postoperatively, finger paint was applied onto the plantar surface of both hind feet of the rats. The rats were allowed to walk down a track, leaving prints of their feet on a paper. From the footprints, the lesion degree was evaluated by the Sciatic Function Index (SFI) using the formula developed by Bain et al. (1989, Plast. Reconstr. Surg. 83: 129) as shown below:

"SFI=−38.3 [(EPL−NPL)/NPL]+109.5[(ETS−NTS)/NTS]+13.3[(EIT−NIT)/NIT]−8.8"

E denotes "experimental";
N denotes "normal";
PL denotes "print length," which refers to the length of hind limb touching the ground, calculated from the tiptoe to the heel;
TS denotes "toe spread," which refers to the distance between the two outermost toes;
EI denotes "intermediary toe spread," which refers to the distance between the two second outmost toes.

Normally, the PL value for an injured limb is higher than that for a normal limb, while the TS and IT values for an injured limb are lower than that for a normal limb. An SFI of 0 is normal while a negative SFI means impairment.

The results are summarized in Table 2 and FIG. 4.

TABLE 2

| Weeks\Group | 1 | 2 | 3 |
|---|---|---|---|
| 2 | −123 | −120.4 | −123.9 |
| 4 | −125.8 | −114.5 | −129.7 |
| 6 | −119.3 | −125.1 | −120.7 |
| 8 | −115.5 | −119.2 | −110.22 |

The results show that the SFI of Group 3 is closest to zero, and thus indicate that the method of the present invention, which utilizes a fibrin glue mixture comprising a growth factor, is helpful in repairing lesions in the peripheral nervous system.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of repairing a nerve root avulsion between a peripheral nerve and the central nervous system in a living vertebrate, the method comprising
   connecting an avulsed end in the peripheral nerve to a portion of the central nervous system through a pia incision, and
   applying to a connection between the avulsed end in the peripheral nerve and the portion of the central nervous system a fibrin glue mixture as the only active agent, the fibrin glue mixture consisting of a growth factor, fibrinogen, aprotinin, and divalent calcium ions so that the fibrin glue mixture is simultaneously in contact with the connection between the avulsed end in the peripheral nerve and the portion of the central nervous system to form an attachment between them.

2. The method of claim 1, wherein portion of the central nervous system is at a nerve root.

3. The method of claim 1, wherein the growth factor is selected from the group consisting of a glial cell line-derived neurotrophic factor, transforming growth factor-beta, fibroblast growth factor, platelet-derived growth factor and epidermal growth factor, vascular endothelial growth factor, and neurotrophin.

4. The method of claim 3, wherein the growth factor is fibroblast growth factor, which is acidic or basic fibroblast growth factor.

5. The method of claim 4, wherein the fibroblast growth factor is acidic fibroblast growth factor.

6. The method of claim 1, wherein components of the fibrin glue mixture can be applied to the gap simultaneously or separately.

7. The method of claim 1, wherein the divalent calcium ions are provided by the addition of calcium chloride or calcium carbonate.

8. The method of claim 1, wherein the fibrin glue mixture consists of fibroblast growth factor, fibrinogen, aprotinin, and calcium chloride.

9. The method of claim 1, wherein the fibrin glue mixture consists of acidic fibroblast growth factor, fibrinogen, aprotinin and calcium chloride.

10. The method of claim 9, wherein the fibrin glue mixture consists of 0.0001-1000 mg/ml of fibroblast growth factor, 10-1000 mg/ml of fibrinogen, 10-500 KIU/ml of aprotinin, and 1-100 mM of calcium chloride.

11. The method of claim 10, wherein the fibrin glue mixture consists of 1 mg/ml of fibroblast growth factor, 100 mg/ml of fibrinogen, 200 KIU/ml of aprotinin, and 8 mM of calcium chloride.

12. The method of claim 1, further comprising anastomosing the other end of the peripheral nerve to a cervical root.

13. The method of claim 12, wherein the fibrin mixture consists of fibroblast growth factor, fibrinogen, aprotinin, and calcium chloride.

14. A method of reconnecting an avulsed end of an intercostal nerve to a cervical root of a spinal cord in a living vertebrate, comprising
   bringing the avulsed end of the intercostal nerve into the cervical root of the spinal cord through a pia incision, and applying to the cervical root of the spinal cord and the avulsed end of the intercostal nerve a fibrin glue mixture as the only active agent, the fibrin glue mixture consisting of a growth factor, fibrinogen, aprotinin, and divalent calcium ions so that the fibrin glue mixture is simultaneously in contact with the avulsed end of the intercostal nerve and the cervical root of the spinal cord to form an attachment between the cervical root and the spinal cord of said vertebrate.

15. The method of claim 14, wherein the growth factor is selected from the group consisting of a glial cell line-derived neurotrophic factor, transforming growth factor-beta, fibroblast growth factor, platelet-derived growth factor and epidermal growth factor, vascular endothelial growth factor, and neurotrophin.

16. The method of claim 15, wherein the growth factor is fibroblast growth factor, which is acidic or basic fibroblast growth factor.

17. The method of claim 16, wherein the fibroblast growth factor is acidic fibroblast growth factor.

18. The method of claim 14, wherein components of the fibrin glue mixture can be applied to the gap simultaneously or separately.

19. The method of claim 14, wherein the divalent calcium ions are provided by the addition of calcium chloride or calcium carbonate.

20. The method of claim 14, wherein the fibrin glue mixture consists of fibroblast growth factor, fibrinogen, aprotinin, and calcium chloride.

21. The method of claim 14, wherein the fibrin glue mixture consists of acidic fibroblast growth factor, fibrinogen, aprotinin, and calcium chloride.

22. The method of claim 21, wherein the fibrin glue mixture consists of 0.0001-1000 mg/ml of fibroblast growth factor, 10-1000 mg/ml of fibrinogen, 10-500 KIU/ml of aprotinin, and 1-100 mM of calcium chloride.

23. The method of claim 22, wherein the fibrin glue mixture consists of 1 mg/ml of fibroblast growth factor, 100 mg/ml of fibrinogen, 200 KIU/ml of aprotinin, and 8 mM of calcium chloride.

24. The method of claim 14, further comprising anastomosing the other end of the intercostal nerve to a cervical root.

25. The method of claim 24, wherein the fibrin mixture consists of fibroblast growth factor, fibrinogen, aprotinin, and calcium chloride.

* * * * *